United States Patent
Xue et al.

(10) Patent No.: US 7,702,382 B2
(45) Date of Patent: Apr. 20, 2010

(54) MULTI-TIER SYSTEM FOR CARDIOLOGY AND PATIENT MONITORING DATA ANALYSIS

(75) Inventors: Joel Q. Xue, Germantown, WI (US); G. Ian Rowlandson, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 454 days.

(21) Appl. No.: 11/405,151

(22) Filed: Apr. 17, 2006

(65) Prior Publication Data

US 2007/0244405 A1 Oct. 18, 2007

(51) Int. Cl.
*A61B 5/02* (2006.01)
(52) U.S. Cl. ...................... 600/509; 600/523
(58) Field of Classification Search .......... 600/508–528
See application file for complete search history.

(56) References Cited

U.S. PATENT DOCUMENTS

| | | | | |
|---|---|---|---|---|
| 4,483,347 | A * | 11/1984 | Wong | 600/525 |
| 5,277,189 | A | 1/1994 | Jacobs | |
| 5,325,856 | A | 7/1994 | Nitzsche et al. | |
| 6,324,423 | B1 | 11/2001 | Callahan et al. | |
| 6,520,910 | B1 * | 2/2003 | Kohls | 600/300 |
| 6,564,090 | B2 | 5/2003 | Taha et al. | |
| 6,616,613 | B1 * | 9/2003 | Goodman | 600/504 |
| 6,665,559 | B2 | 12/2003 | Rowlandson | |
| 6,875,174 | B2 * | 4/2005 | Braun et al. | 600/300 |
| 2002/0165459 | A1 | 11/2002 | Starobin et al. | |
| 2003/0200114 | A1 * | 10/2003 | Ogino et al. | 705/2 |
| 2005/0115561 | A1 * | 6/2005 | Stahmann et al. | 128/200.24 |

FOREIGN PATENT DOCUMENTS

| | | |
|---|---|---|
| EP | 1 190 672 A2 | 3/2002 |
| EP | 1 529 487 A1 | 5/2005 |

OTHER PUBLICATIONS

GB Search Report dated Aug. 13, 2007.

* cited by examiner

*Primary Examiner*—Carl H Layno
*Assistant Examiner*—Brian T Gedeon
(74) *Attorney, Agent, or Firm*—Andrus, Sceales, Starke & Sawall, LLP (57) ABSTRACT

In a multi-tier patient monitoring data analysis system, an algorithm server is positioned as a middle tier between an acquisition device, such as a cardiograph or patient monitor that can be seen as a lower tier, and a storage device for a database, such as that of a central computer for a hospital or clinic that can be seen as an upper tier. The algorithm server gathers current data from the real time acquisition device and obtains previously stored ECG signal data from the database. The algorithm server contains ECG analysis algorithm(s) and runs one or more algorithms using the current and previously acquired ECG signal data. Analysis algorithms may also be run on the acquisition device. The system provides the rapid, extensive, and thorough ECG analysis that is critical to patient welfare.

17 Claims, 12 Drawing Sheets

Interpretation: Sig. ST change
ST trend:
T trend:
Intra-QRS trend:

Interpretation: New LBBB
ST: ST up 2mm in Ant ld
T: T inv (5mm) in Inferior ld
QRS: 100 – 120 msec

MULTI-TIER SYSTEM FOR CARDIOLOGY AND PATIENT MONITORING DATA ANALYSIS

FIELD OF THE INVENTION

The present invention relates to a multi-tier system for cardiology and patient data analysis in which an algorithm server is interposed between a real time ECG signal data acquisition device, such as a cardiograph, and a database of stored cardiology information.

BACKGROUND OF THE INVENTION

Electrocardiography employs the electrical phenomena accompanying the physiological functioning of the heart for diagnostic and other purposes. Electrodes are applied to the chest and extremities of a patient to collect electrocardiographic (ECG) signal data and provide same to an acquisition unit, typically an electrocardiograph or patient monitor. The signals in the electrodes are amplified in a pre-amplifier and are typically displayed on a screen and/or moving paper strip for review and analysis by an attending cardiologist or other clinician. The ECG signal data is also digitized for storage in a memory and for use with computer ECG analysis algorithms.

However, only a limited amount of ECG signal data is often available for use with such acquisition apparatus, such as the data obtained during a single session with the patient. Acquisition apparatus such as a patient monitor, may carry out other tasks or functions besides ECG monitoring. This may limit the computing power available for ECG analysis, necessitating a reduction in a sophistication of an analysis algorithm in the monitor or slowing the analysis process. This limits the type of analysis that can be performed and the thoroughness with which it can be carried out. For example, if real time shape analysis of the heart beat waveforms found in the ECG signal data is desired, this may require transfer of the signal data from the acquisition unit to separate analysis apparatus containing a more sophisticated algorithm. Given the often critical nature of electrocardiological conditions, the limitations and delays attendant the foregoing give rise to the potential for adverse consequences to the patient.

In another example, in a chest pain clinic, a convenient, rapid serial comparison of currently obtained ECG signal data with previously acquired ECG signal data is essential to determine if there has been a change in the cardiac condition of the patient. However, in most cases, the previously acquired ECG signal data is stored in a remote database, such as the central computer for the clinic or hospital. Currently, it is thus often necessary to load the ECG signal data from the cardiograph or patient monitor into different apparatus, such as central clinic or hospital computer, having the database in which the previously acquired ECG signal data is stored. Thereafter, the serial comparison may be run. It will be appreciated that this can be an inconvenient and/or time consuming process, to the detriment to the patient.

To avoid or limit such consequences, rapid, extensive, and thorough ECG analysis is critical to patient welfare. Inconveniences associated with such analyses should be minimized to encourage the use of pertinent algorithms and/or to avoid affecting the accuracy of the ECG data analysis and interpretation, also to prevent detriment to the patient.

SUMMARY OF THE INVENTION

An embodiment of the present invention overcomes the foregoing, and other, shortcomings by providing a multi-tier system in which an algorithm server is positioned as a middle tier between an acquisition device, such as a cardiograph, patient monitor, or patient-side terminal linked to the current ECG signal data that can be seen as a lower tier, and a storage device for a database, such as that of a central computer server for a hospital or clinic, that can be seen as an upper tier. The algorithm server gathers current data from the real time acquisition device and obtains previously stored ECG signal data from the database thus providing a link between the real time ECG signal data and the stored ECG signal data. The algorithm server can also obtain other related medical information from different databases, such as a hospital information system (HIS). The algorithm server may contain a plurality of ECG algorithms and runs one or more of the algorithms using the current and previously acquired ECG signal data and clinical information such as patient medical history.

The multi-tier system of the present invention provides rapid, thorough analysis and interpretation of ECG signal data and can provide a plurality of different analyses. The multi-tier structure enables the system to have a much better scalability, i.e. the ability to handle a wide range of requirements demanded by differing users. Another advantage is that because the algorithms are stored and run in the middle tier algorithm server, there will minimum disruption to the operation of the database that, as noted above, often comprises the central computer for a hospital or clinic that serves numerous other functions. Still another advantage is that consistent versions of the algorithms will be running on the algorithm server, whereas with separate acquisition or other devices, different versions of software may be running on different devices.

The invention will be further understood by reference to the following detailed description taken in conjunction with the drawing.

DETAILED DESCRIPTION

Figure 1:
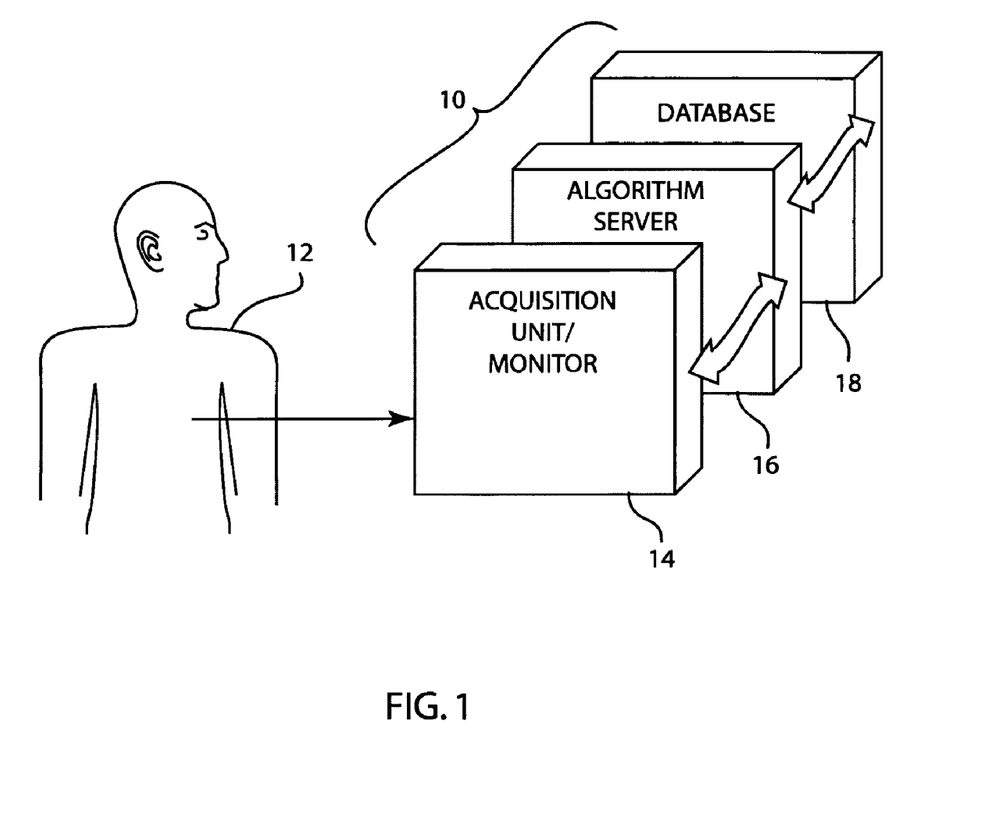
FIG. 1 is a generalized schematic diagram of a multi-tier system of the present invention for cardiology and patient monitoring data analysis.

An embodiment of system 10 of the present invention for the analysis and interpretation of ECG signal data obtained from patient 12 comprises of a multi-tier arrangement of an acquisition unit 14, algorithm server 16, and database 18, as shown diagrammatically in FIG. 1.

Figure 2:
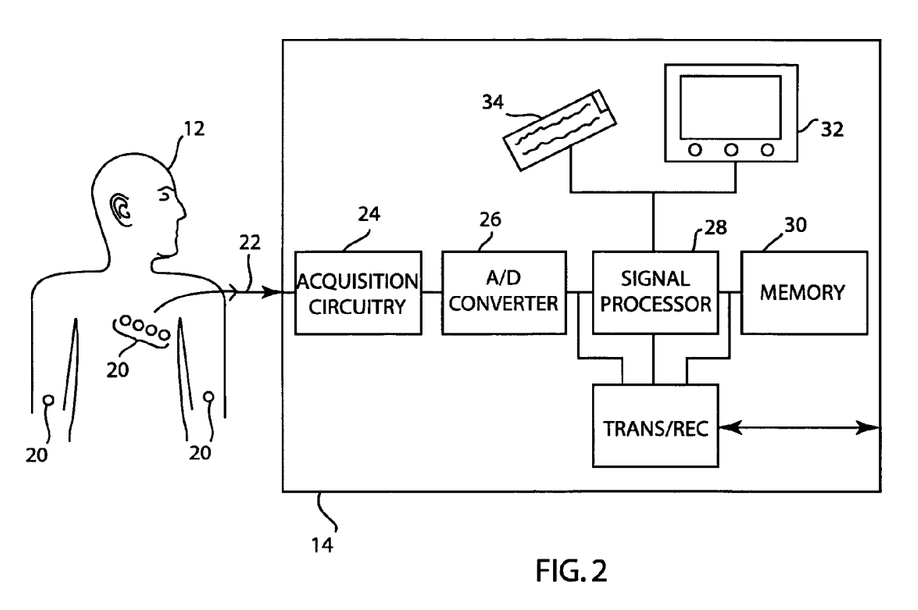
FIG. 2 is a detailed schematic diagram of an acquisition unit for use in the system of the present invention.

As shown in FIG. 2, acquisition unit 14 is coupled to electrodes 20 applied to the chest and extremities of patient 12. Acquisition unit 14 acquires real time ECG signal data via patient connection cable 22. Selected pairs of electrodes, or leads, are used to acquire standard, multiple lead electrocardiographic signal data. Acquisition unit 14 may be a device such as a cardiograph, a bedside patient monitor, a Holter patient monitor, or other suitable monitor. Acquisition unit 14 can also be a portable/handheld device embedded into a cellular phone, electronic messaging unit, personal data organizer, pager, and the like.

Acquisition unit 14 includes acquisition circuitry 24 for carrying out initial processing of the ECG signal data, such as lead connection quality determination, filtering, pre-amplification, and the like. Acquisition circuitry 24 also includes analog-digital conversion circuitry 26 for converting the analog ECG data signals in cable 22 to digitized signals.

Acquisition circuitry 24 is connected to signal processor 28 having a central processing unit for controlling the operation of acquisition unit 14 and performing the processing or other use of the signal data carried out in acquisition unit 14. Memory 30 for storing ECG signal data is coupled to signal processor 28. Acquisition unit 14 may also include display 32 for providing a graphic and/or textual showing of the electrocardiographic signal data. Display 32 typically comprises a cathode ray tube, liquid crystal display, or other suitable apparatus for providing a visually perceptible indication of the data. Alternatively, or additionally, a printer provides a paper copy 34 of the ECG data in strip or sheet form. Acquisition unit 14 also includes transmitter/receiver 36 that transmits information from, and receives information for, acquisition unit 14.

Acquisition unit 14 is connected to algorithm server 16. Algorithm server 16 may comprise a computer server, for example, that manufactured sold by the General Electric Healthcare unit of the General Electric Co. under the designation "Muse." Server 16 contains computer algorithms, programs, or other instructions for carrying out desired analyses and interpretation of ECG signal data. Algorithm server 16 preferably contains a plurality of ECG algorithms so as to allow use of different algorithms to obtain different results or to combine results, thereby to obtain a more robust cardiac analysis of the patient.

Algorithm server 16 is connected to the storage device for database 18. Database 18 may be contained in a central, or mainframe, computer for a health services provider, such as a hospital or clinic. Database 18 may comprise a component of a hospital information system (HIS). Or, database 18 may comprise a dedicated database for system 10. Previously obtained ECG signal data, as well as other patient information, is stored in database 18.

The connections between the components of system 10 may be wired or wireless. Or the connection may be effected through a computer network, such as a secure local area network (LAN) or wireless LAN, a secure wide area network (WAN) or wireless WAN or a secure internet connection. It is also possible for algorithm server 16 and the storage device for database 18 to form components of the same computer server unit.

FIGS. 3A-3E diagrammatically show one manner of operation of system 10. The operation is shown as a real-time ischemic monitoring of multi-lead ECG signal data. Such an operation may typically be carried out in a chest pain clinic to assist in determining the presence of a condition, such as acute myocardial infarction or acute cardiac ischemia, in patients suffering severe chest pain. The operation is initiated by a request to the system, either at one of the components or through a link to/from a remote location such as a cardiology laboratory.

Figure 3A:
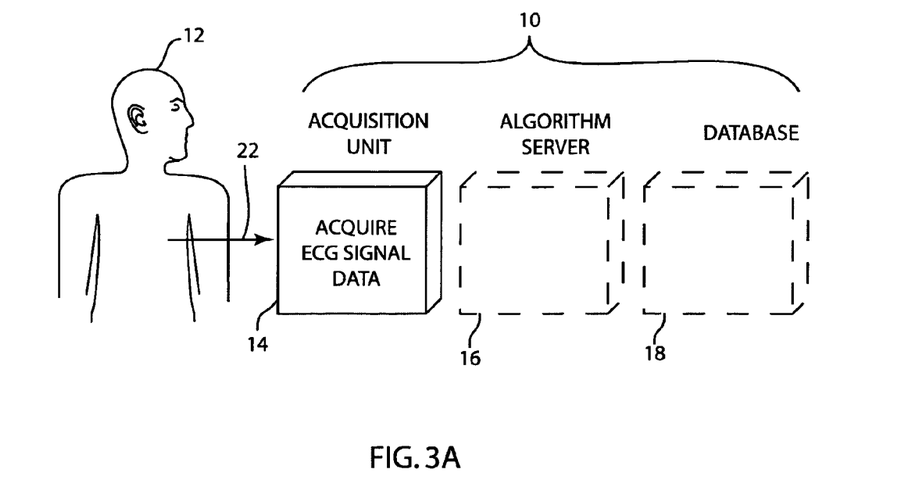
FIGS. 3A-3E shows the operation of the system of the present invention in carrying out real-time patient monitoring data analysis.
Figure 3B:
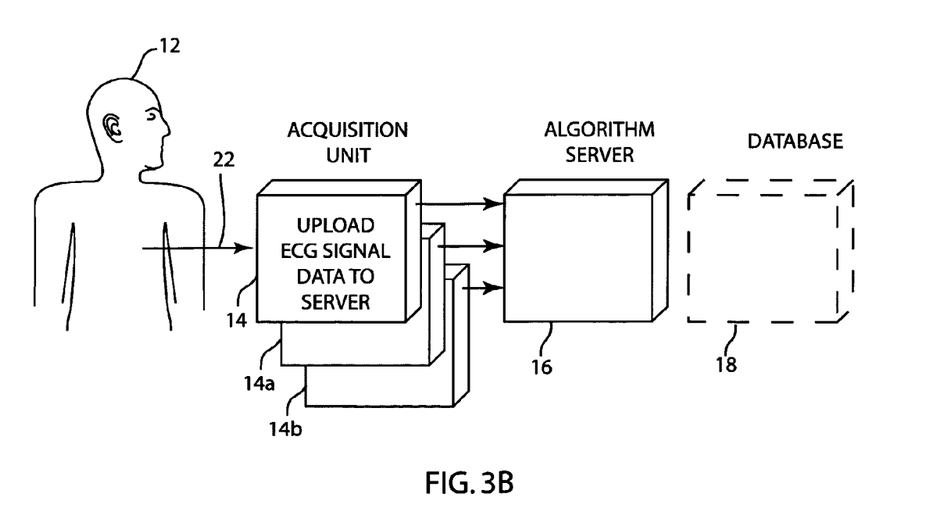
Figure 3C:
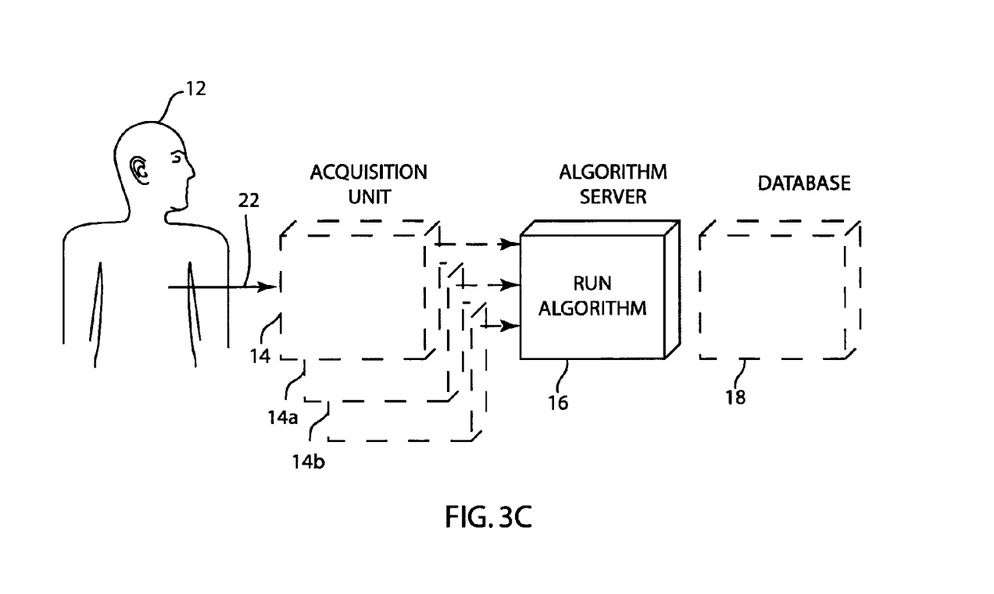

As shown in FIG. 3A, in carrying out such an analysis and determination with system 10 of the present invention, acquisition unit 14 acquires ECG. signal data from patient 12 via cable 22. The signal data will typically be 12/15 lead ECG signal data. After the initial processing of the acquired real time data in acquisition circuitry 24 and/or signal processor 28 of acquisition unit 14, the ECG signal data is uploaded to algorithm server 16, as shown in FIG. 3B. As shown in FIG. 3B, it will be appreciated that in a facility such as a chest pain clinic, or hospital unit in which cardiac monitoring is carried out for numerous patients, a plurality of acquisition units 14a, 14b, 14c may be in communication with algorithm server 16.

Figure 3D:
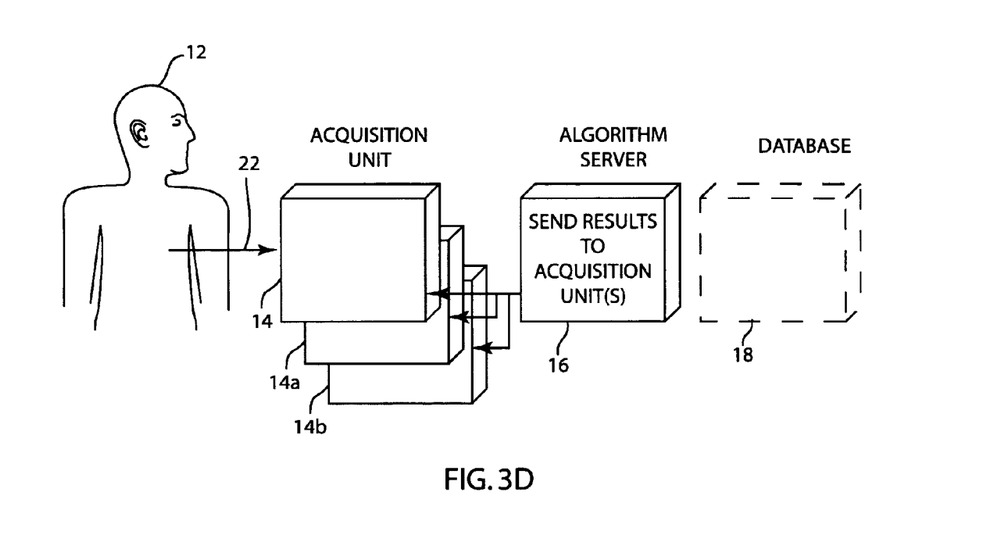
Figure 3E:
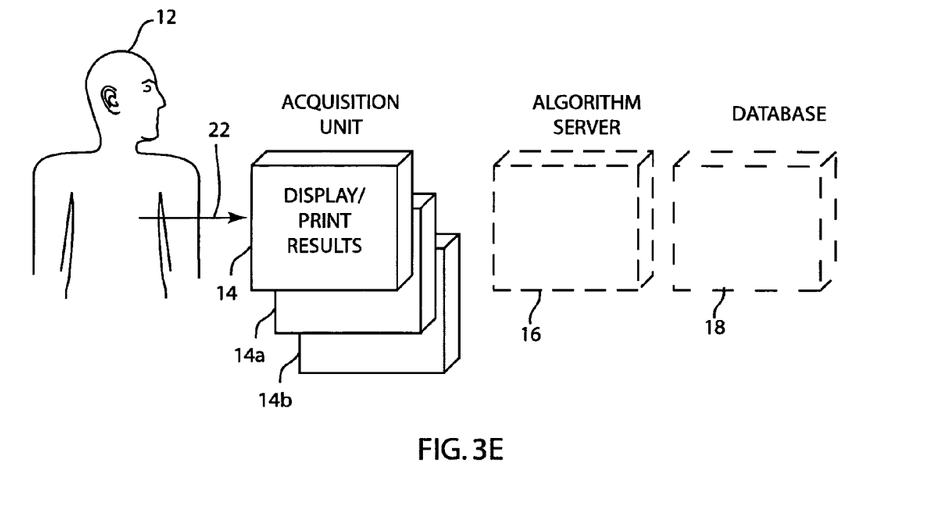
Figure 4:
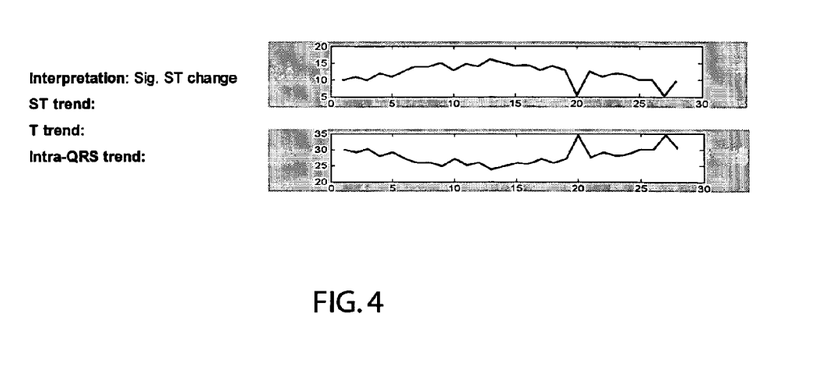
FIG. 4 is a display of monitoring data produced by the operation of the system illustrated in FIGS. 1 through 3.

Algorithm server 16 then runs the appropriate computer algorithm to process the ECG signal data received from data acquisition unit(s) 14. See FIG. 3C. In an example, the algorithm may be a tracing algorithm that continuously traces the morphology of the acquired ECG signal data. Following completion of the running of the algorithm, the results may be sent back to acquisition unit(s) 14, as shown in FIG. 3D, and displayed in display 32 or 34 of the acquisition unit(s) or at some other appropriate location in the clinic or hospital. See FIG. 3E. A typical example of a display produced by an ECG morphology tracing algorithm in algorithm server 16 is shown in FIG. 4 that shows a display of continuous ST-T wave monitoring.

FIGS. 5A-G show a further use for multi-tier system 10. Specifically, FIG. 5 shows a use of system 10 in carrying out real-time serial comparison of electrocardiographic data. Such a comparison is also often employed in a chest pain clinic for monitoring patients for a condition such as acute myocardial infarction or acute cardiac ischemia. FIGS. 5A-5G show use of multi-tier system 10 in which two-way data flows occur between algorithm server 16 and an acquisition unit or units 14 and data flow also occurs between algorithm server 16 and one or more databases 18. After algorithm server 16 obtains real-time data from acquisition unit(s) 14 and previously stored data from database 18, algorithm server 16 can run different types of algorithms for providing a desired analysis of electrocardiographic data, and either send the results back to acquisition unit(s) 14 or/and to database 18. The analysis results and original data from acquisition unit(s) 14 can also be sent to attending clinicians if immediate care is needed.

Figure 5A:
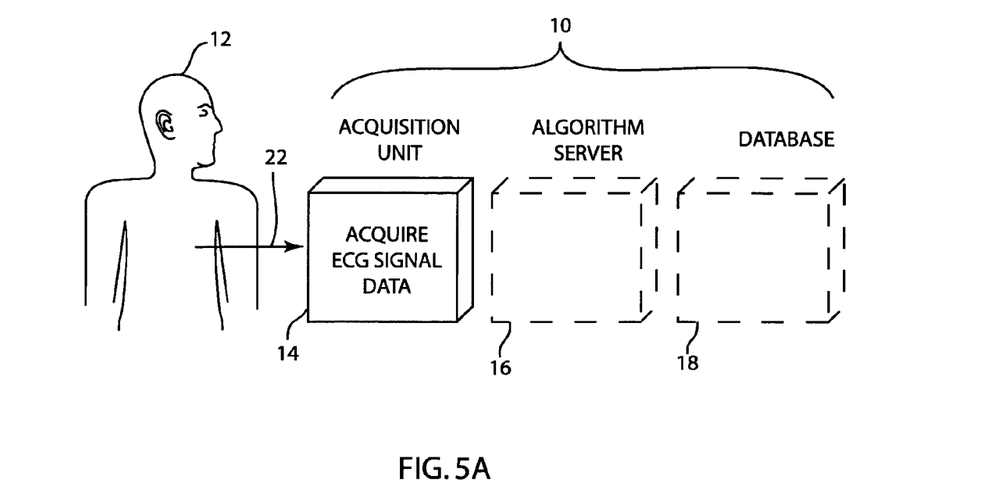
FIGS. 5A-5G show a use of the multi-tier patient monitoring data. analysis system of the present invention employing two-way data flows between the algorithm server and an acquisition unit and a database.
Figure 5B:
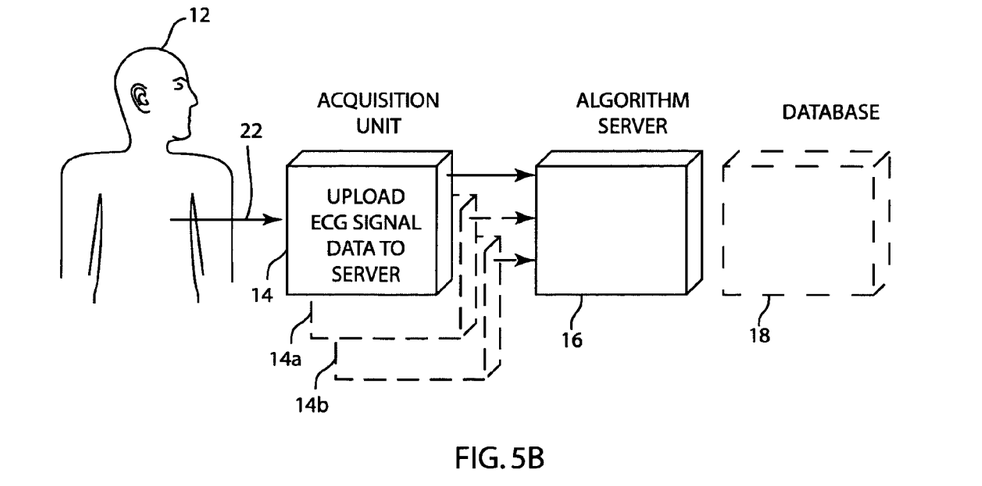
Figure 5C:
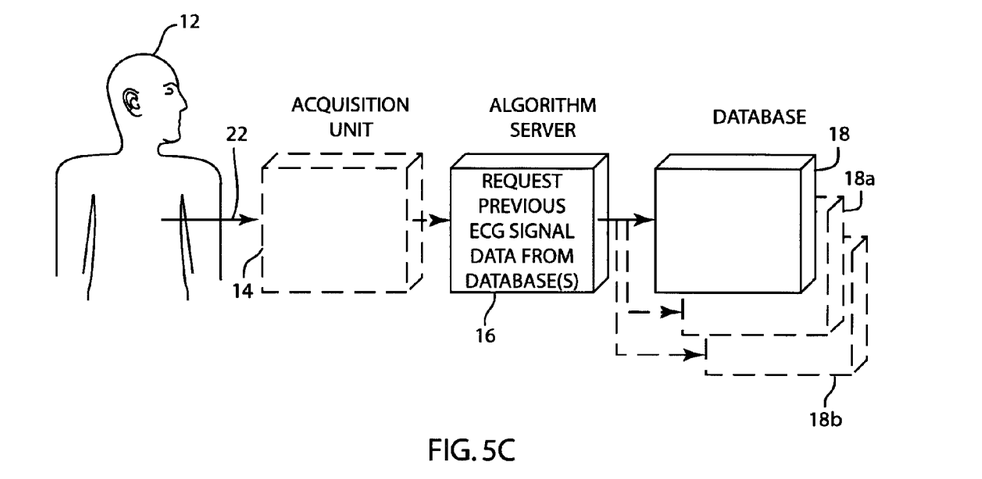
Figure 5D:
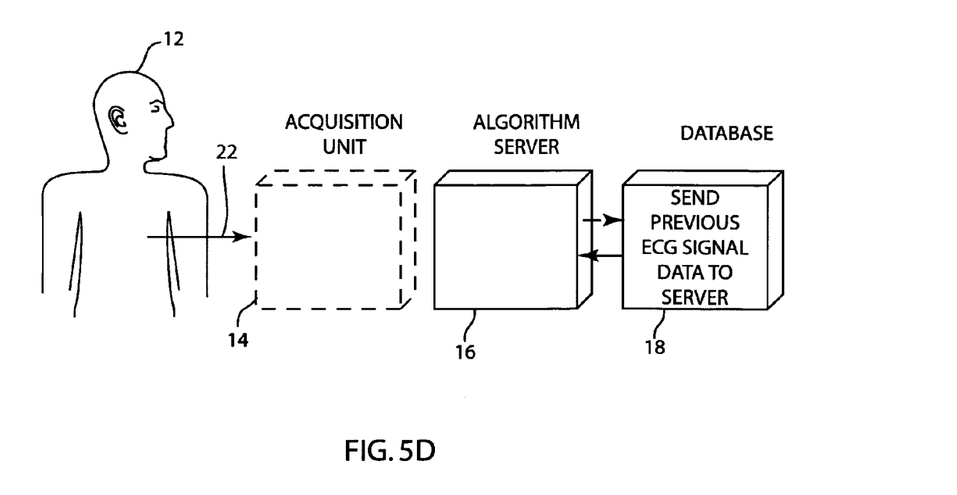

As shown in FIG. 5A, in such an application, data acquisition unit 14 acquires real time ECG signal data from patient 12 via ECG cable 22. In FIG. 5B, the ECG signal data from acquisition unit or units 14 is uploaded to algorithm server 16. For purposes of carrying out the comparison of ECG data, algorithm server 16 requests electrocardiographic data previously obtained from patient 12 from the storage device for database 18. The requested ECG data will typically be that taken from an immediately previous electrocardiographic examination of patient 12 but any stored ECG signal data desired by a clinician may be obtained from database 18. The request of data from database 18 by algorithm server 16 is shown in FIG. 5C and the sending of the previously obtained ECG signal data by database 18 to algorithm server 16 is shown in FIG. 5D. FIG. 5C notes that the previously obtained signal data may be found in, and obtained from, a number of database locations 18, 18a, 18b, etc.

Figure 5E:
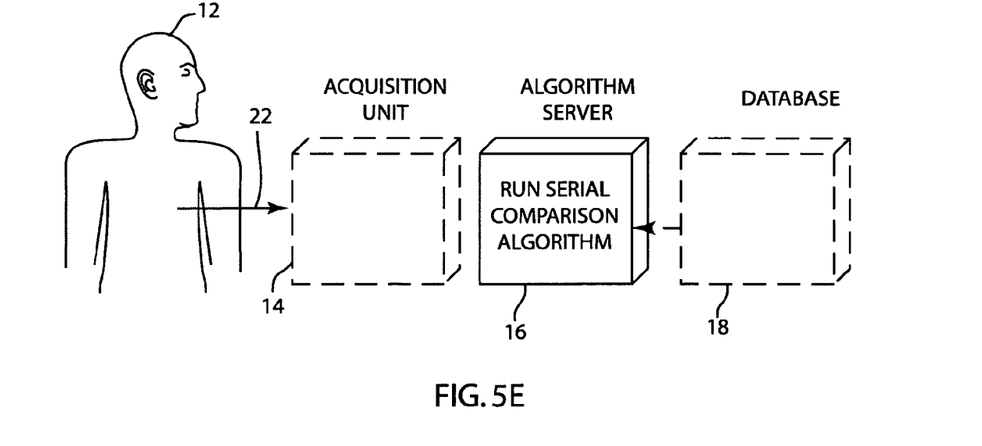
Figure 5F:
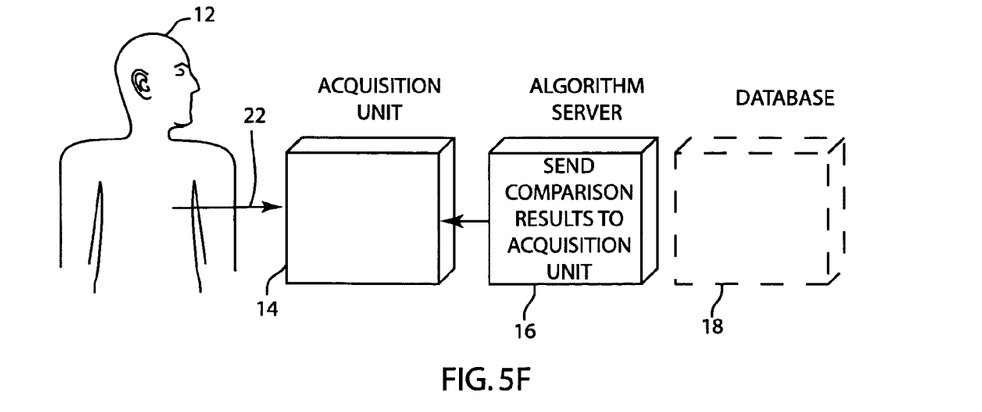
Figure 5G:
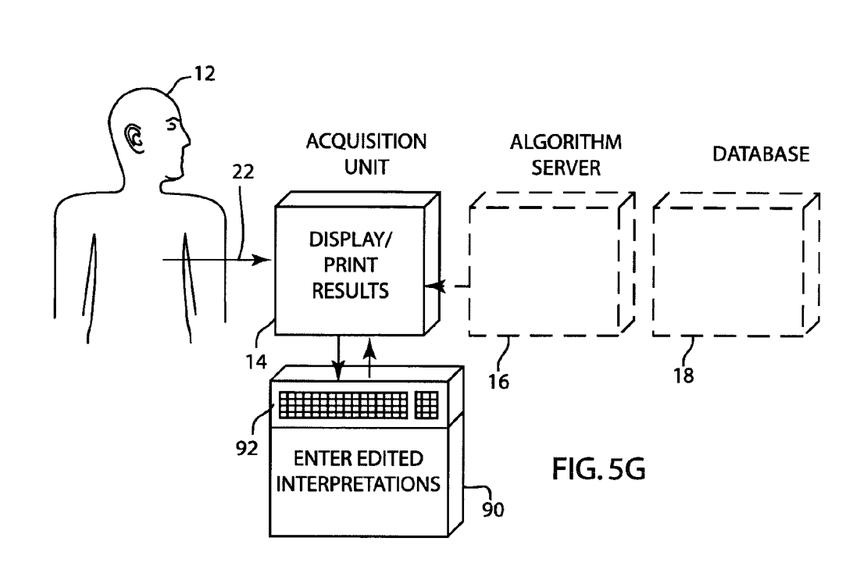

Thereafter, algorithm server 16 runs a serial comparison algorithm, as shown in FIG. 5E to compare the morphology and other aspects of the most recent ECG signal data obtained from the patient with the previous ECG signal data obtained from the patient. The comparison results may then sent to a suitable device for review by a cardiologist or other clinician. FIG. 5G shows the use of acquisition unit 14 to display and/or print out the results for this purpose but any suitable display, such as a cardiac laboratory workstation may be used to review the results.

The processes shown in FIGS. 5A-5G proceed in real-time, i.e. as the ECG signal data from patient 12 is received, thus resulting in an acceleration of the process of analyzing and interpreting the ECG signal data and diagnosing the cardiac condition of patient 12. The process may be repeated as needed or at fixed intervals so that any changes in the cardiac condition of the patient with time will become apparent.

Figure 6:
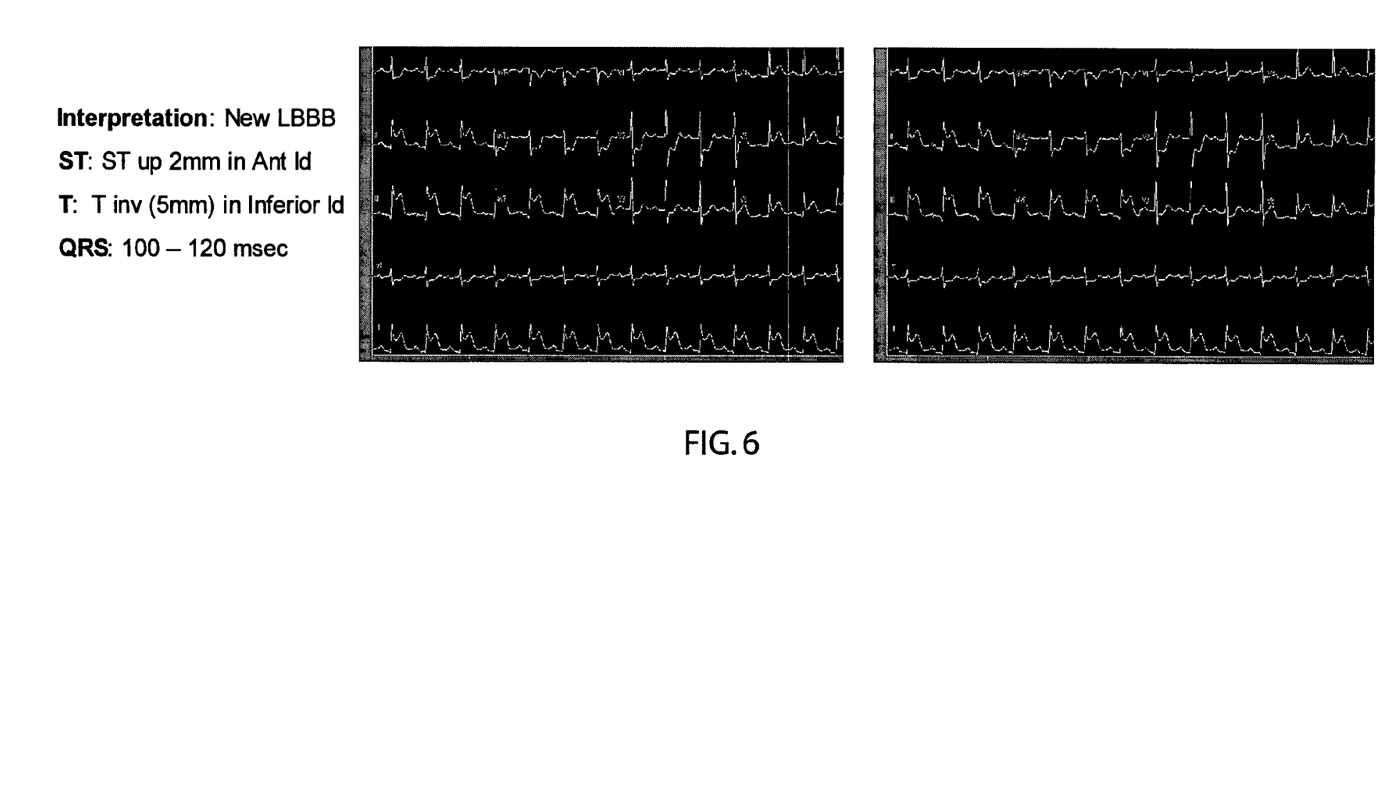
FIG. 6 shows a display generated by the apparatus, as used in the manner shown in FIG. 5.

FIG. 6 shows a typical serial ECG comparison report generated by algorithm server 16 operating in the manner of FIG. 5E and that can be displayed on acquisition unit 14.

The algorithm or program contained in algorithm server 16 may be one that allows a clinician, following review of the results produced by ECG algorithm, to provide data or edited interpretations to one or both of acquisition unit 14 or server 16. See FIG. 5G at 90. For example, this allows the operation of apparatus 10 to pull forward a previous diagnosis made by the algorithm in server 16, or portions of previous diagnosis, if there has been no significant change in the electrocardiographic data from patient 10, as determined by the data comparison. Such a program also permits use of a previous detection of the P-wave portion of the electrocardiographic data in order to improve current rhythm detection. The provision of data or edited interpretations may be provided by an appropriate data entry device, such as keyboard 92 shown in FIG. 5G.

Figure 7A:
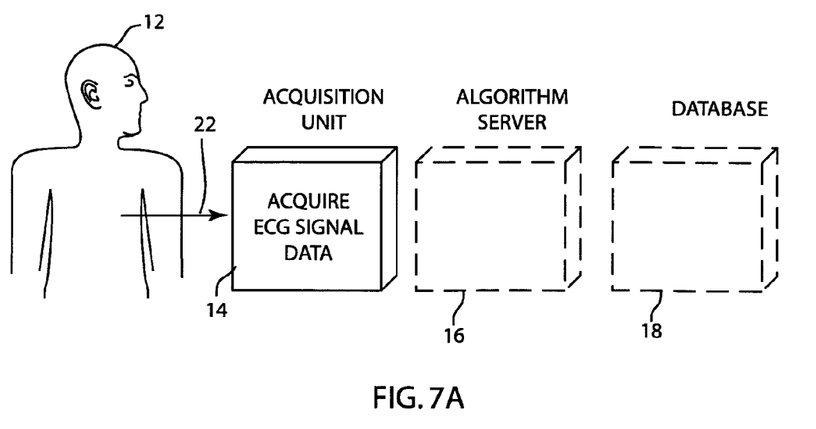
FIGS. 7A-7E show operation of the system of the present invention in which algorithms are run in both the acquisition unit and algorithm server and in which ECG data can be over-read and/or edited.
Figure 7B:
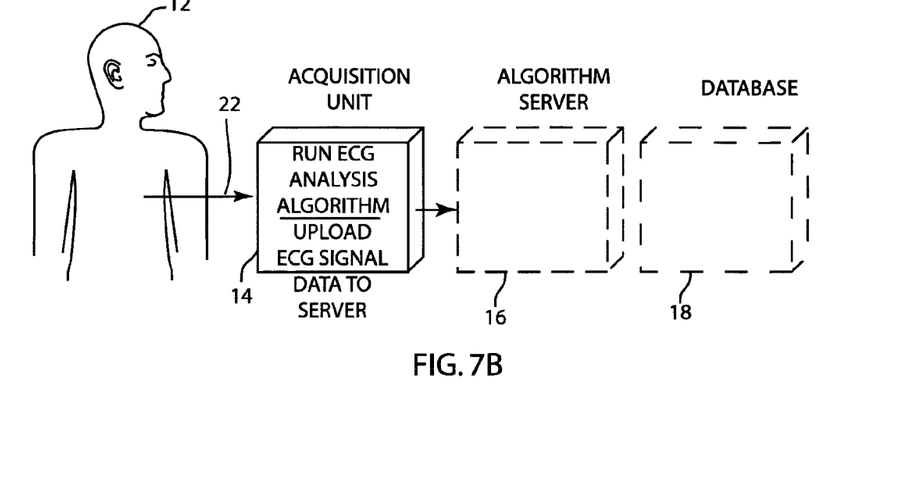

FIG. 7A-7E shows an operation of system 10 in a manner in which acquisition unit 14 runs one ECG algorithm and algorithm server 16 runs a different ECG analysis or interpretation algorithm. As shown in FIG. 7A, acquisition unit 14 acquires an electrocardiographic data from patient 12 via an ECG cable 22. In FIG. 7B, acquisition unit 14 employs signal processor 28 to run an algorithm, such as real-time heart beat or arrhythmia detection algorithm stored in the signal processor.

Figure 7C:
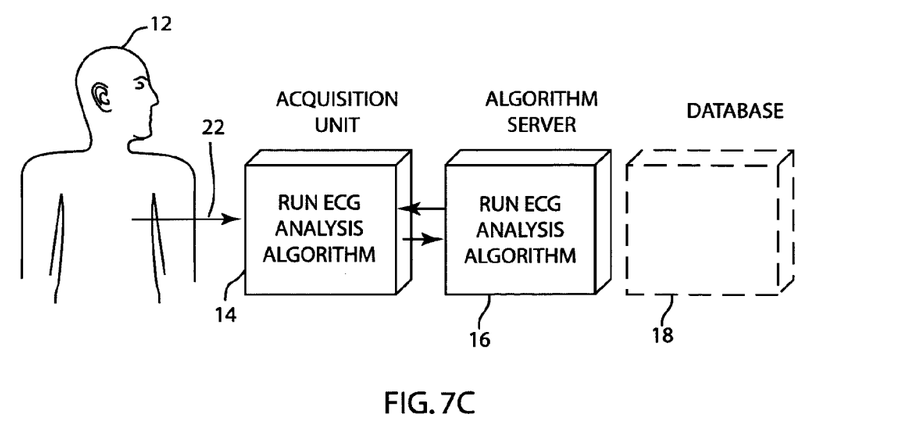
Figure 7D:
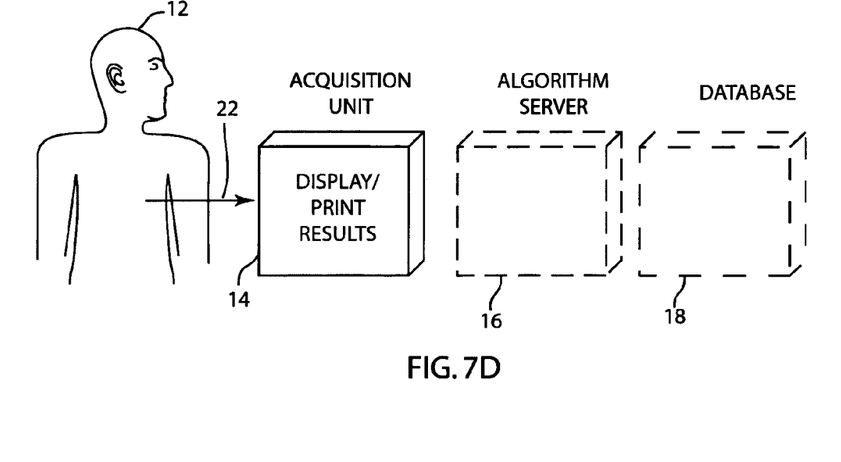
Figure 7E:
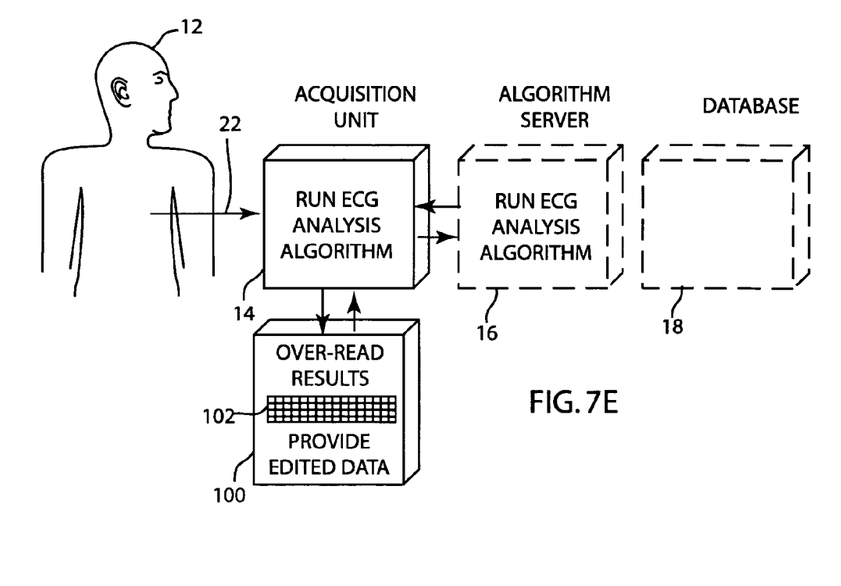

Also as shown in FIG. 7B, acquisition unit 14 uploads ECG signal data to algorithm server 16. As shown in FIG. 7C, algorithm server 16 runs a different ECG analysis algorithm than that being run in acquisition unit 14. For example, algorithm server 16 may run a real-time shape analysis algorithm. The data analysis results obtained from the running of the two computer programs can be provided to the clinician for a more accurate diagnosis of the cardiac condition of patient 12 as shown in FIG. 7D. The shape analysis information obtained from the analysis carried out by the algorithm in server 16 can improve the real-time beat arrhythmia analysis performed by the algorithm running in acquisition unit 14.

In addition to embodiments of system 10 in which algorithms are run in algorithm server 18 and additionally in acquisition/monitor unit 14, system 10 of the present invention may use other data than the real-time signal data obtained from acquisition unit 14. For example, additional data may be obtained from database 18 in the manner shown in FIGS. 5C and 5D. Such additional data may, for example, comprise that derived from a population of patients.

In addition to utilizing data stored in database 18, apparatus 10 may also use information entered by a clinician utilizing apparatus 10. As shown by block 100 of FIG. 7E, the clinician reads the displayed graphic or text ECG results relating to the rhythm and shape of the electrocardiographic data. The clinician then inputs interpreted data into acquisition unit 14 by device 102 for use in the algorithm running in acquisition unit 14 and/or the algorithm running an algorithm server 16. Such an over-reading improves the overall accuracy of the determinations made by apparatus 10, as well as confirming the accuracy of computerized ECG interpretations made by the algorithms in algorithm server 16 and acquisition unit 14.

Other examples of the use of edited interpretation for patient monitoring include real-time arrhythmia analysis based on edited interpretation. In this application, an overall edited arrhythmia is cataloged for improving arrhythmia recognition carried out in acquisition unit 14. Examples of edited arrhythmias that could improve computerized recognition of arrhythmia conditions include learning the R-R interval patterns from a segment of historical ECG signal data and real-time sampled ECG signal data so that atrial fibrillation can be properly identified. The R-R interval is the time interval occurring between the prominent R peaks of the QRS portion of successive heart beat waveforms in the ECG data. Another example of edited arrhythmias include verification of pace rhythms and the corresponding rate so that they are properly identified during future episodes of pacing. Still further, editing may be used for verification of rate dependent conduction abnormalities so that this arrhythmia may be properly labeled by acquisition unit 14.

Another example is a real time contour analysis based on edited interpretation. In this application, the overall edited contour of the waveforms in the ECG signal data is cataloged for improving the contour recognition carried out in data acquisition unit 14. For example, various intervals occurring in the ECG waveforms, such as the Q-T interval, the P-R interval, and the duration of the QRS complex may be measured and confirmed so that future beats are properly recognized and measured. Similarly, the identification of repolarization abnormalities that are not the result of an acute process such as those typical of left ventricular hypertrophy with strain can be used, particularly as reference measurements for improving contour recognition. Or, identification of significant S-T interval deviation including the point of measure, such as J+60, J+80, etc. may be edited so that it can be recognized in future episodes. Contour recognition may also be employed to determine the effect of certain drugs on the Q-T interval of the waveforms of the ECG signal data.

A further non-limiting list of examples of edited information that could be entered in system 10 to improve the computerized analysis performed by the algorithms in data acquisition unit 14 and/or algorithm server 16 includes the following related to ECG morphology: double detection of the QRS feature of the electrocardiographic data fixed by correct labeling of the T-wave portion of the electrocardiographic data; verification of coupling intervals for premature ventricular contractions (PVCs) so that artifacts that occur with different coupling intervals are more likely to be recognized as artifacts; correct identification of P-wave morphology, or template, for subsequent atrial detections; correct identification of artificially paced beats so that the algorithms of algorithm server 16 or acquisition unit 14 do not indicate idioventricular rhythms; correct identification of right bundlebranch block (RBBB) or left bundlebranch block (LBBB), so that beats can be called aberrantly conducted versus ectopic; proper identification of Q-T interval so that trending can be based on edited measurements; and proper identification of the P-R interval so that trending of first degree atrioventricular (AV) block can be done based on an edited measurement.

While system 10 of the present invention has been described in connection with FIG. 7 with a single ECG analysis algorithm running in algorithm server 16, it will be appreciated that, as noted above, multiple algorithms may be used and the results and features combined together to improve the accuracy of the single detection and interpretation. For example, for continuous 12 lead ECG data, it is possible to run 12 lead ECG interpretation, heart-rate-variability, and T-wave-alternans algorithms at the same time on algorithm server 16.

Various alternatives and embodiments are contemplated as being within the scope of the following claims particularly pointing out and distinctly claiming the subject matter regarded as the invention.

What is claimed is:

1. A system for electrocardiographic data analysis and display comprising:
   an acquisition unit connected to the patient by a plurality of sensors that collect physiological data from the patient, the acquisition unit including a signal processor that performs real-time data analysis on the collected physiological data, and further including a graphical display that presents the results of the real-time data analysis;
   a database comprising stored patient physiological data, the stored patient physiological data being historical data previously collected from the patient;
   an algorithm server that receives the collected physiological data from the acquisition unit and the stored patient physiological data from the database, the algorithm server having a plurality of data analysis algorithms and applying at least one algorithm of the plurality to the collected physiological data and the stored physiological data to create results data, the results data being transmitted to the acquisition unit and being displayed on the graphical display; and
   a communications network communicatively connecting the acquisition unit, the database and the algorithm server to facilitate the transfer of data between the acquisition unit, the database and the algorithm server;
   wherein the acquisition unit processes the collected physiological data in real time according to a first analysis algorithm and the algorithm server processes the collected physiological data in real time according to a second analysis algorithm, the first analysis algorithm being different from the second algorithm.

2. A system according to claim 1 further defined as comprising a plurality of acquisition units connected to said algorithm server.

3. A system according to claim 1 wherein said acquisition unit is a Holter recorder.

4. A system according to claim 1 wherein the communications network is a wireless communications network.

5. A system according to claim 1 wherein the communications network is a secure local area network.

6. A system according to claim 1 wherein the acquisition unit further comprises a data entry device that facilitates the entry of user observations and the editing of the collected physiological data.

7. A system according to claim 1 wherein a common apparatus comprises both said database and said algorithm server.

8. A system according to claim 1 wherein at least one algorithm of the plurality of data analysis algorithms comprises a serial ECG comparison algorithm, the algorithm server applying the serial ECG comparison algorithm to the received collected physiological data and the received stored patient physiological data, to produce results data.

9. A system according to claim 8 wherein the serial ECG comparison algorithm comprises an ECG signal data morphology comparison algorithm.

10. The system of claim 9 wherein the stored patient physiological data is physiological data previously collected from the patient.

11. The system of claim 10 wherein the stored patient physiological data is edited by a clinician to create an edited interpretation of an ECG morphology pattern.

12. A system according to claim 8 wherein the serial ECG comparison algorithm comprises an arrhythmia analysis algorithm.

13. The system of claim 1, wherein the acquisition unit further comprises a memory, the memory storing and buffering the collected physiological data such that collected physiological data is stored prior to being transmitted to the algorithm server.

14. The system of claim 1, wherein the first analysis algorithm is an arrhythmia detection algorithm and the second analysis algorithm is an ECG shape analysis algorithm.

15. A system for physiological data analysis and display comprising:
   an acquisition unit connected to the patient with a plurality of sensors that collect physiological data from the patient, the acquisition unit including a signal processor that performs real-time data analysis on the collected physiological data, and further including a graphical display that presents the results of the real-time data analysis;
   a database comprising stored patient physiological data, the stored patient physiological data being historical data previously collected from the patient;
   an algorithm server that receives the collected physiological data and the results of the real-time data analysis from the acquisition unit and the stored patient physiological data from the database, the algorithm server having a plurality of data analysis algorithms and applying at least one algorithm of the plurality to the collected physiological data, the results of the real-time data analysis, and the stored physiological data to create results data, the results data being transmitted from the algorithm server to the acquisition unit for display on the graphical display; and
   a communications network communicatively connecting the acquisition unit, the database and the algorithm server to facilitate the transfer of data between the acquisition unit, the database and the algorithm server;
   wherein the acquisition unit processes the collected physiological data in real time according to a first analysis algorithm and the algorithm server processes the collected physiological data in real time according to a second analysis algorithm, the first analysis algorithm being different from the second analysis algorithm; and
   wherein the graphical display of the acquisition unit presents both the real-time data analysis and the results data.

16. The system of claim 15, wherein at least one algorithm of the plurality of data analysis algorithms comprises a serial data comparison algorithm, the serial data comparison algorithm comparing the received collected physiological data to the received stored patient physiological data.

17. A system for physiological data analysis and display comprising:
   an acquisition unit connected to the patient with a plurality of sensors that collect physiological data from the patient, the acquisition unit including a signal processor that performs real-time data analysis on the collected physiological data, and further including a graphical display that presents the results of the real-time data analysis;

a database comprising a stored patient physiological data, the stored patient physiological data being historical data previously collected from the patient;

an algorithm server that receives the collected physiological data and the results of the real-time date analysis from the acquisition unit and the stored patient physiological data from the database, the algorithm server having a plurality of data analysis algorithms, at least one algorithm of the plurality comprising a serial data comparison algorithm, the serial data comparison algorithm comparing the received collected physiological data to the received stored patient physiological data, and applying one algorithm of the plurality to the collected physiological data, the results of the real-time data analysis, and the stored physiological data to create results data, the results data being transmitted from the algorithm server to the acquisition unit for display on the graphical display, and a communications network communicatively connecting the acquisition unit, the database, and the algorithm server to facilitate the transfer of data between the acquisition unit, the database, and the algorithm server;

wherein the graphical display of the acquisition unit presents both real-time data analysis and the results data, and wherein the stored patient physiological data is an edited interpretation of previously collected patient physiological data.

* * * * *